United States Patent [19]
Biziere et al.

[11] Patent Number: 5,378,706
[45] Date of Patent: Jan. 3, 1995

[54] FUSED-THIAZOLE DERIVATIVES ACTIVE ON THE CHOLINERGIC SYSTEM, AND PHARMACEUTICAL COMPOSITIONS CONTAINING SAME

[75] Inventors: Kathleen Biziere, Riedisheim; Dominique Olliero, Montpellier; Paul Worms, Saint-Gely du Fesc, all of France

[73] Assignee: Sanofi, Paris, France

[21] Appl. No.: 68,224

[22] Filed: May 28, 1993

Related U.S. Application Data

[60] Division of Ser. No. 632,609, Dec. 27, 1990, Pat. No. 5,232,921, which is a continuation of Ser. No. 167,291, Mar. 11, 1988, abandoned.

[30] Foreign Application Priority Data

Mar. 12, 1987 [FR] France .................. 87 03398

[51] Int. Cl.$^6$ ............... C07D 277/84; C07D 417/12; C07D 401/12; A61K 31/425
[52] U.S. Cl. .................. 514/232.8; 514/255; 514/321; 514/342; 514/366; 514/338; 546/209; 546/270; 546/280; 544/133; 544/367
[58] Field of Search ........... 544/133, 135, 367; 546/270, 280, 209; 548/150; 514/232.8, 255, 321, 338, 342, 366, 367

[56] References Cited

U.S. PATENT DOCUMENTS

| | | | |
|---|---|---|---|
| 4,064,244 | 12/1977 | Sorg | 514/371 |
| 4,241,072 | 12/1980 | Bolhofer | 514/252 |
| 4,517,196 | 5/1985 | Schlecker et al. | 544/245 |

OTHER PUBLICATIONS

Chem. Abstracts, vol. 75(21), Abst. No. 129,703-J dated Nov. 22, 1971.

*Primary Examiner*—Alan L. Rotman
*Attorney, Agent, or Firm*—Foley & Lardner

[57] ABSTRACT

The invention relates to thiazole derivatives corresponding to the general formula:

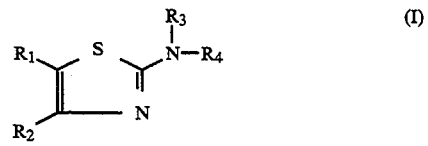

in which:
- $R_1$ and $R_2$ each independently represent hydrogen; a $C_1$-$C_4$ alkyl group; a phenyl group or a phenyl group monosubstituted or polysubstituted by a halogen atom, a $C_1$-$C_4$ alkyl group, a $C_1$-$C_4$ alkoxy, nitro or hydroxyl group; or one of the groups $R_1$ and $R_2$ denotes hydrogen and the other represents a naphthyl group; a benzyl group; an α,α-dimethyl-benzyl group; a cyclohexyl group; a biphenyl group; a thienyl group or an adamantyl group; or alternatively $R_1$ and $R_2$, taken together, represent a group;

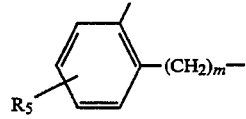

in which the phenyl group is bonded to the 4-position of the thiazole and the group $(CH_2)_m$ to the 5-position, m represents an integer equal to 2 or 3 and $R_5$ denotes hydrogen or a nitro group, $R_3$ is H or an alkyl group and $R_4$ is notably an alkyl substituted by an amino group, a pyrrolidino, or a pydridino group.

10 Claims, No Drawings

FUSED-THIAZOLE DERIVATIVES ACTIVE ON THE CHOLINERGIC SYSTEM, AND PHARMACEUTICAL COMPOSITIONS CONTAINING SAME

This application is a divisional of application Ser. No. 07/632,609, filed on Dec. 27, 1990, U.S. Pat. No. 5,232,921, which is a continuation of Ser. No. 07/167,291, filed Mar. 11, 1988, abandoned.

The present invention relates to novel thiazole derivatives, a process for their preparation and their application in therapy.

According to a first aspect, the invention relates, by way of novel products, to thiazole derivatives corresponding to the general formula:

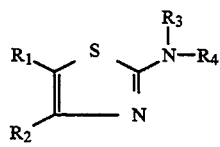

(I)

in which:
- $R_1$ and $R_2$ each independently represent hydrogen; a $C_1$-$C_4$ alkyl group; a phenyl group or a phenyl group monosubstituted or polysubstituted by a halogen atom, preferably chlorine or fluorine, by a $C_1$-$C_4$ alkyl group, preferably the methyl group, or by a $C_1$-$C_4$ alkoxy, nitro or hydroxyl group; or one of the groups $R_1$ and $R_2$ denotes hydrogen and the other represents a naphthyl group; a benzyl group; an α,α-dimethyl-benzyl group; a cyclohexyl group; a biphenyl group; a thienyl group or an adamantyl group; or alternatively $R_1$ and $R_2$, taken together, represent a group:

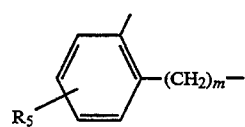

in which the phenyl group is bonded to the 4-position of the thiazole and the group $(CH_2)_m$ to 5-position, and in which m represents an integer equal to 2 or 3 and $R_5$ denotes hydrogen or a nitro group occupying one of the free positions on the ring, with the proviso that if one of the groups $R_1$ or $R_2$ denotes hydrogen, the other is different from H or methyl;
- $R_3$ represents hydrogen or a $C_1$-$C_4$ lower alkyl group; and
- $R_4$ represents:
  - a group:

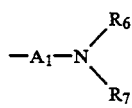

in which $A_1$ denotes a linear or branched $C_2$-$C_5$ alkyl group and $R_6$ and $R_7$, taken independently, represent hydrogen, a $C_1$-$C_4$ alkyl group or $C_3$-$C_6$ cycloalkyl group, or alternatively $R_6$ and $R_7$, taken with the nitrogen atom to which they are bonded, form a 5-membered or 6-membered heterocycle optionally containing a second heteroatom, and especially the pyrrolidine, piperidine, morpholine and N-alkylpiperazine rings;
  - a group:

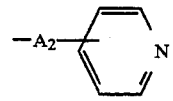

in which $A_2$ denotes a group $(CH_2)_m$, where m=0, 1, 2 or 3, which substitutes the pyridine ring in the 2-, 3- or 4-position;
  - a group:

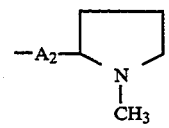

in which $A_2$ is as indicated above; or
  - a group:

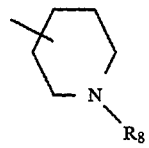

in which $R_8$ denotes a $C_1$-$C_4$ alkyl group; or alternatively the substituent

represents a group:

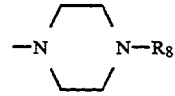

in which $R_8$ is as indicated above, and also their addition salts with mineral or organic acids.

If the substitutent $R_4$ contains an asymmetric carbon atom, the compounds (I) exist in the form of 2 optical isomers. These optical isomers form an integral part of the invention.

According to a second aspect, the invention relates to a process for the preparation of the compounds of formula (I).

The process for the preparation of the thiazole derivatives as hereinabove defined comprises the steps of heating in an acid medium of pH 1 to 6, a substituted thiourea of the formula:

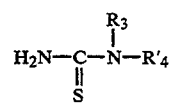

in which $R_3$ has the meaning indicated above and $R'_4$ has the same meanings as $R_4$ except in cases where $R_4$ contains a primary or secondary amine, when $R'_4$ denotes the group corresponding to $R_4$ in which a hydrogen belonging to the said amine group has been replaced by a protective group which is resistant to hydrolysis in an alkaline medium, with an alpha-brominated carbonyl derivative of the formula:

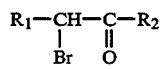

or with the corresponding bromine derivative in which the carbonyl group is protected in the form of an acetal, to give the compounds (I), and of converting the compound I to a salt, if desired, by a known process.

The substituted thiourea used in the invention process can be obtained by conventional processes, for example by action of a benzoyl isothiocyanate or a pivaloylisothiocyanate on a primary amine 1.

If $R_3$ is hydrogen, this process can be represented by the following reaction scheme:

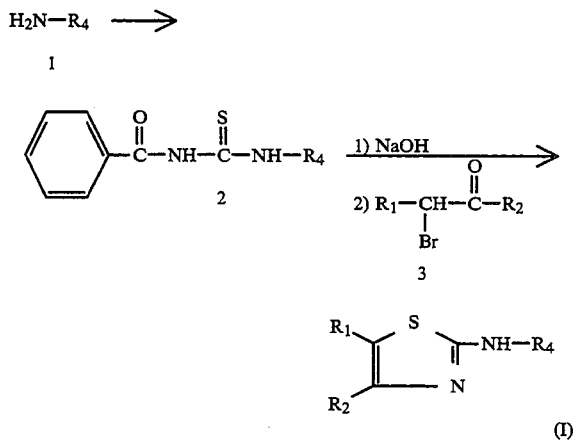

Reaction of benzoyl isothiocyanate with the primary amine 1 gives the substituted benzoylthiourea 2.

In practice, the benzoyl isothiocyanate is formed in situ by reacting benzoyl chloride with potassium thiocyanate in a solvent such as anhydrous acetone.

A solution of the amine derivative 1 in a suitable solvent, especially methylene chloride, is added to the resulting solution of benzoyl isothiocyanate and the mixture is heated at a temperature between 50° C. and 100° C. for ½ to 3 hours.

After removal of the solvents, the reaction mixture is taken up in water and the product 2 is isolated in the usual way, either by solvent extraction and purification, or by chromatography, or by direct crystallization.

The product (I) is obtained in 2 steps from the benzoylthiourea.

First of all, the benzoyl group is removed by heating the compound 2 with a dilute aqueous solution of sodium hydroxide. The reaction mixture is acidified by the addition of an acid, for example concentrated hydrochloric acid up to a pH between 1 and 6, after which a solution of the bromine derivative 3 in a water-miscible solvent, preferably an alcohol, is added.

The mixture is heated for a few hours at a temperature between 70° and 100° C.

After evaporation of the solvents, the reaction mixture is taken up in a solution of sodium bicarbonate or carbonate and the product (I) is isolated by extraction with a solvent such as methylene chloride.

After purification by the usual methods, the compound (I) is converted to a salt, if desired, by reaction with an acid in accordance with a known process.

In this process, if the bromine derivative 3 is not very stable or not readily available, it can be replaced with the corresponding dimethylacetal.

Finally, if $R_4$ contains a primary or secondary amine group, it has to be blocked in order to avoid a side-reaction with the benzoyl chloride. It is possible to use a protective group which is resistant to hydrolysis in an alkaline medium, such as for example a tert.butoxycarbonyl group(Boc).

The corresponding benzoylthiourea 2 is obtained from the amine $R_4NH_2$ protected in this way. Reaction with dilute sodium hydroxide removes the benzoyl group and direct reaction with the bromine derivative 3 at an acid pH causes the formation of the thiazole ring and the removal of the group Boc, leading to the compounds (I) in which $R_4$ contains a primary or secondary amine group.

The starting materials 1 and 3 are known compounds or can be prepared by known processes. Processes for obtaining compounds 3 are notably disclosed by HOUBEN WEYL "Methoden der Organischen Chemie" 4th edition, vol. 4/5 p. 171–188-Georg Thieme Verlag.

In the particular case where $R_4$ represents a group:

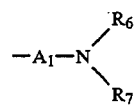

in which at least one of the substituents $R_6$ and $R_7$ is hydrogen, the protected amine derivatives 1 can be prepared from the aminonitrile $R_7NH$—$A'_1$—CN. When treated with the anhydride $(Boc)_2O$, this gives the aminonitrile

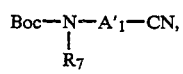

which, on reduction, leads to the corresponding primary amine

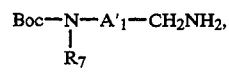

in which $A'_1$ represents $A_1$ minus a methylene group.

In all cases, and particularly if the substituent $R_3$ is other than hydrogen, the compounds (I) can be prepared from pivaloyl isothiocyanate according to the scheme:

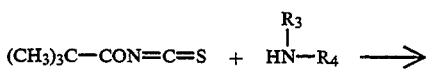

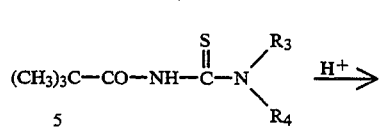

-continued $$H_2N-\overset{\overset{S}{\|}}{C}-\overset{\overset{R_3}{|}}{N}-R_4 \longrightarrow (I)$$
6

Reaction of pivaloyl isothiocyanate with the amine 4 gives the pivaloylthiourea 5.

In practice, the pivaloyl isothiocyanate is formed in situ by reacting pivaloyl chloride with an alkali metal thiocyanate in an anhydrous solvent, such as acetone, and at a moderate temperature (0° to 10° C.). The amine 4 is then added and the mixture is left to react for a few hours at the same temperature.

The compound 5 is deacylated by hydrolysis under the action of heat in a strong acid medium, giving the thiourea 6.

This is converted to the compound (I) by reaction with a bromine derivative 3, as indicated previously.

The non-limiting examples which follow will provide a clearer understanding of the invention.

EXAMPLE 1:

2-[(2-Diethylaminoethyl)amino]-5-phenylthiazole dihydrochloride (SR 44318 A)

A) N-Benzoyl-N'-(diethylaminoethyl)thiourea

A solution of 70 ml of benzoyl chloride in 100 ml of anhydrous acetone is added dropwise, at room temperature, to a suspension of 51 g of potassium thiocyanate in 300 ml of anhydrous acetone. When the addition is complete, the reaction mixture is refluxed for 5 minutes. A solution of 85 ml of 2-diethylaminoethylamine in 100 ml of methylene chloride is added slowly to the resulting hot solution, with vigorous stirring, so as to keep the mixture under reflux. When the addition is complete, the mixture is stirred for 1 hour at room temperature, the solvents are then evaporated off and the residue is taken up in iced water. Extraction is carried out twice with 200 ml of methylene chloride and the solution is dried over magnesium sulfate. The solvent is evaporated off to dryness and the oily product obtained is purified by chromatography on a silica column. Impurities of low polarity are removed by elution with an 80/20 (vol/vol) methylene chloride/ethyl acetate mixture. The expected product is then obtained by elution with a 95/5 (vol/vol) methylene chloride/methanol mixture.

Weight: 78 g; m.p.: 54°-56° C.

B) SR 44318 A 3.5 g of the compound prepared above are refluxed in 18 ml of a 2.5N solution of sodium hydroxide under a nitrogen atmosphere for 30 minutes. After cooling, concentrated hydrochloric acid is added until the pH is about 6. A solution of 2.48 g of alpha-bromophenylacetaldehyde in 25 ml of 95° ethanol is added and the mixture is refluxed for 1 hour under a nitrogen atmosphere.

It is evaporated in vacuo and a 10% aqueous solution of sodium carbonate is added. Extraction is carried out twice with methylene chloride and the solution is dried over magnesium sulfate. The solvent is evaporated off and the residue is chromatographed on a silica column by elution with a 95/5 (vol/vol) methylene chloride/methanol mixture, giving an oil (1.46 g).

This oil is dissolved in anhydrous ether, a solution of hydrogen chloride in anhydrous ether is added and the mixture is left to crystallize. The crystals are filtered off, washed with anhydrous ether and dried in vacuo.
M.p.: 178° C.

EXAMPLES 2 TO 108:

A) The substituted thioureas collated in Table 1 below are obtained by following the procedure of Example 1-A but varying the amine compounds used.

TABLE 1

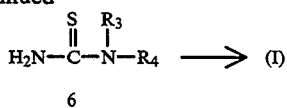

| $R_4$ | Physical constant |
|---|---|
| (CH$_2$)$_2$—N(morpholino) | M.p. = 119-120° C. |
| (CH$_2$)$_3$—N(C$_2$H$_5$)$_2$ | Oil, TLC: Rf = 0.51 CH$_2$Cl$_2$/MeOH 90/10 vol/vol |
| (CH$_2$)$_3$—N(CH$_3$)$_2$ | M.p. = 67-69° C. |
| (CH$_2$)$_3$—N(morpholino) | Oil |
| (CH$_2$)$_2$—N(piperidino) | M.p. = 98-99° C. |
| (CH$_2$)$_2$—N(pyrrolidino) | M.p. = 70-71° C. |
| (CH$_2$)$_2$—N((CH$_2$)$_3$CH$_3$)$_2$ | M.p. = 48-49° C. |
| (CH$_2$)$_2$—N(CH(CH$_3$)$_2$)$_2$ | M.p. = 93-94° C. |
| (CH$_2$)$_4$—N(C$_2$H$_5$)$_2$ | Oil |
| (CH$_2$)$_2$—N-methylpyrrolidinyl | M.p. = 65-67° C. |

TABLE 1-continued

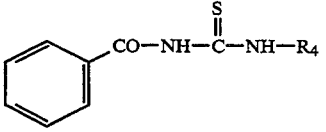

| R4 | Physical constant |
|---|---|
| 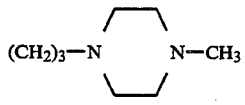 | M.p. = 55–57° C. |
| 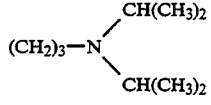 | Oil |
| 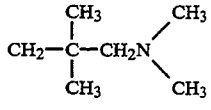 | M.p. = 57–58° C. |
| 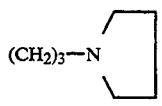 | M.p. = 73–75° C. |
| 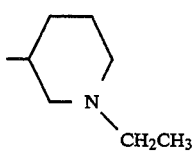 | Oil |
| 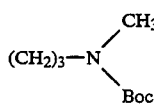 | M.p. = 72–74° C. |
| 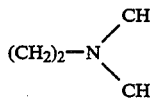 | M.p. = 74–75° C. |
| 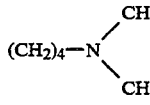 | M.p. = 31–35° C. |
| 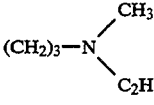 | Oil |
| 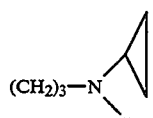 | M.p. = 45–48° C. |

TABLE 1-continued

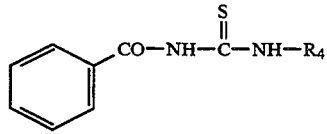

| R4 | Physical constant |
|---|---|
| 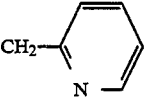 | M.p. = 152–153° C. |
| 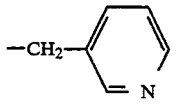 | M.p. = 98–100° C. |
| 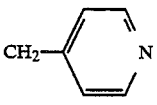 | M.p. = 158–159° C. |
| 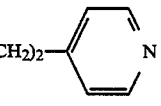 | M.p. = 146–147° C. |
| 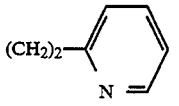 | M.p. = 118–119° C. |
| 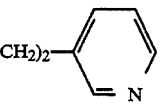 | M.p. = 142–143° C. |
| 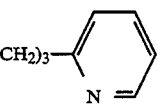 | M.p. = 81–82° C. |
| 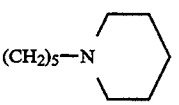 | M.p. = 118–120° C. |

B) The products of formula (I) collated in Table 2 below are obtained by following the procedure of Example 1-B, starting from these different thioureas and varying the oxohalogen derivative reacted therewith.

TABLE 2

$$\underset{R_2}{\overset{R_1}{>}}\!\!=\!\!\underset{N}{\overset{S}{>}}\!\!-\!\!NH\!-\!R_4$$

| Ex. no. | SR code no. | $R_1$ | $R_2$ | $R_4$ | Salt M.p. °C. (solvent) |
|---|---|---|---|---|---|
| 2 | 44244 A | H | phenyl | $-(CH_2)_2-N$(morpholine) | Dihydrochloride 220–221 (iPrOH/Et$_2$O) |
| 3 | 44284 A | " | " | $-(CH_2)_3-N$(morpholine) | Dihydrochloride 216–217 (iPrOH) |
| 4 | 44285 A | phenyl | H | $-(CH_2)_2-N$(morpholine) | Dihydrochloride 264–265 (iPrOH/EtOH 95) |
| 5 | 44286 A | H | phenyl | $-(CH_2)_2-N(C_2H_5)_2$ | Succinate 110–111 (iPrOH/iPr$_2$O) |
| 6 | 44345 A | " | " | $-(CH_2)_3-N(CH_3)_2$ | Dihydrochloride 181–182 (Et$_2$O) |
| 7 | 44346 A | phenyl | H | $-(CH_2)_3-N(C_2H_5)_2$ | Dihydrochloride 0.5H$_2$O 143–144 (acetone) |
| 8 | 44347 A | H | 2,4,6-trimethylphenyl | $-(CH_2)_3N(C_2H_5)_2$ | Dihydrochloride 199–200 (cyclohexane, Et$_2$O) |
| 9 | 44372 A | " | " | $-(CH_2)_2N(C_2H_5)_2$ | Dihydrochloride 1H$_2$O 147–148 (acetone, Et$_2$O) |
| 10 | 44373 A | phenyl | $-CH_3$ | $-(CH_2)_3N(C_2H_5)_2$ | Dihydrochloride 0.5H$_2$O 184-5 (acetone, Et$_2$O) |
| 11 | 44374A | H | phenyl | " | Dimaleate 109–111 (iPrOH, Et$_2$O) |
| 12 | 44421 A | H | 2,4,6-trimethylphenyl | $-(CH_2)_3-N(CH_3)_2$ | Dihydrochloride 224–226 (iPrOH, Et$_2$O) |

TABLE 2-continued $$\underset{R_2}{\overset{R_1}{>}}\!\!=\!\!\underset{N}{\overset{S}{\underset{\|}{\bigvee}}}\!\!\!\text{NH}\!-\!R_4$$

| Ex. no. | SR code no. | R₁ | R₂ | R₄ | Salt M.p. °C. (solvent) |
|---|---|---|---|---|---|
| 13 | 44422 A | H | —CH₃ | —(CH₂)₂—N(C₂H₅)₂ | Dihydrochloride 162–163 (iPrOH, Et₂O) |
| 14 | 44424 A | H | 2,4-dichlorophenyl | —(CH₂)₂—N(piperidine) | Dihydrochloride 216–217 (iPrOH, Et₂O) |
| 15 | 44434 A | —CH₃ | phenyl | —(CH₂)₃—N(C₂H₅)₂ | Dihydrochloride 0.5H₂O 148–149 (iPrOH, Et₂O) |
| 16 | 44435 A | phenyl | phenyl | —(CH₂)₃—N(C₂H₅)₂ | Dihydrochloride 0.5H₂O 167–168 (iPrOH, iPr₂O) |
| 17 | 44436 A | " | —CH₃ | —(CH₂)₂N(C₂H₅)₂ | Dihydrochloride 0.5H₂O 154–155 (Et₂O) |
| 18 | 44437 A | phenyl | phenyl | —(CH₂)N(C₂H₅)₂ | Dihydrochloride 193–194 (Et₂O) |
| 19 | 44438 A | " | H | —(CH₂)₂—N(pyrrolidine) | Dihydrochloride 0.5H₂O 190–195 (dec) (Et₂O) |
| 20 | 44451 A | H | 4-fluorophenyl | —(CH₂)₂—N((CH₂)₃CH₃)₂ | Dihydrochloride 141–142 (Et₂O, PrOH) |
| 21 | 44465 A | H | 2-methoxyphenyl | —(CH₂)₃—N(CH₃)₂ | Dihydrochloride 184–186 (dec) (iPrOH, Et₂O) |
| 22 | 44466 A | phenyl | —CH₃ | —(CH₂)₂—N(piperidine) | Dihydrochloride 204–207 (dec) (iPrOH) |
| 23 | 44467 A | phenyl | —CH₃ | —(CH₂)₃—N(CH₃)₂ | Dihydrochloride 235–236 (dec) (iPrOH, iPr₂O) |

TABLE 2-continued

R₁, R₂, R₄ substituents on structure shown (S, NH-R₄, N).

| Ex. no. | SR code no. | R₁ | R₂ | R₄ | Salt M.p. °C. (solvent) |
|---|---|---|---|---|---|
| 24 | 44468 A | H | 1-adamantyl | $-(CH_2)_2-N(C_2H_5)_2$ | Dihydrochloride 196–199 (iPrOH, iPr₂O) |
| 25 | 44469 A | H | 4-NO₂-C₆H₄– | $-(CH_2)_2-N(C_2H_5)_2$ | Dihydrochloride 185–190 (dec) (iPrOH, Et₂O) |
| 26 | 44488 A | C₆H₅– | –CH₃ | $-(CH_2)_2-$pyrrolidinyl | Dihydrochloride 178–180 (Et₂O) |
| 27 | 44489 A | " | " | $-(CH_2)_2-N(CH(CH_3)_2)_2$ | Dihydrochloride 1H₂O 130–135 (iPrOH, iPr₂O) |
| 28 | 44490 A | " | H | $-(CH_2)_2-$piperidinyl | Dihydrochloride 250 (dec) (Et₂O) |
| 29 | 44491 A | " | H | $-(CH_2)_2-N(CH(CH_3)_2)_2$ | Dihydrochloride 1H₂O 93 (Et₂O) |
| 30 | 44492 A | " | H | $-(CH_2)_2-N((CH_2)_3CH_3)_2$ | Dihydrochloride 147 (acetone, Et₂O) |
| 31 | 44493 A | H | 4-Cl-C₆H₄– | $-(CH_2)_3-N(CH_3)_2$ | Dihydrochloride 1H₂O 141 (iPrOH, iPr₂O, H₂O) |
| 32 | 44494 A | H | 4-F-C₆H₄– | $-(CH_2)_3-N(CH_3)_2$ | Dihydrochloride 1H₂O 114 (iPrOH, Et₂O) |
| 33 | 44515 A | C₆H₅– | –CH₂–C₆H₅ | $-(CH_2)_3-N(C_2H_5)_2$ | Dihydrochloride 1H₂O 88–89 (Et₂O) |
| 34 | 44516 A | H | 2-naphthyl | $-(CH_2)_2-$piperidinyl | Dihydrochloride 1H₂O 91–93 (Et₂O) |

TABLE 2-continued structure: R₁, R₂ on vinyl with S attached, C(=N)NH—R₄

| Ex. no. | SR code no. | R₁ | R₂ | R₄ | Salt M.p. °C. (solvent) |
|---|---|---|---|---|---|
| 35 | 44573 A | H | 2-naphthyl | —(CH₂)₃—N(C₂H₅)₂ | Dihydrochloride 96° C. (Et₂O) |
| 36 | 44574 A | H | cyclohexyl | —(CH₂)₃—N(CH₃)₂ | Dihydrochloride 155° C. (Et₂O/iPrOH) |
| 37 | 44575 A | H | 2-thienyl | —(CH₂)₂—N-morpholino | Dihydrochloride 182° C. (EtOH 95/iPrOH) |
| 38 | 44576 A | H | 2,4,6-trimethylphenyl | —(CH₂)₅—N-piperidino | Dihydrochloride 150–155 (Et₂O) |
| 39 | 44749 A | H | 2,4-dichlorophenyl | —(CH₂)₃—N(CH₃)₂ | Dihydrochloride 194–196° C. (Et₂O) |
| 40 | 44750 A | H | " | —(CH₂)₄—N(C₂H₅)₂ | Fumarate 121–3° C. (Et₂O) |
| 41 | 44768 A | H | 4-biphenylyl | —(CH₂)₃—N(C₂H₅)₂ | Fumarate 182–4° C. (Et₂O) |
| 42 | 44769 A | CH₃ | phenyl | —(CH₂)₃—N(CH₃)₂ | Dihydrochloride 191° C. (Et₂O) |

TABLE 2-continued

Structure: $R_1$ and $R_2$ on carbon double-bonded to C(S)(NH-$R_4$)=N

| Ex. no. | SR code no. | $R_1$ | $R_2$ | $R_4$ | Salt M.p. °C. (solvent) |
|---|---|---|---|---|---|
| 43 | 44770 A | H | 2,4-difluorophenyl | " | Dihydrochloride (1H$_2$O) 168° C. (Et$_2$O) |
| 44 | 44786 A | H | 4-fluorophenyl | $-(CH_2)_2-$N-methylpyrrolidin-2-yl | Difumarate 138–140° C. (Et$_2$O) |
| 45 | 44791 A | H | 3-nitrophenyl | $-(CH_2)_3-N(CH_3)_2$ | Dihydrochloride (0.5H$_2$O) 175–6° C. (Et$_2$O) |
| 46 | 44814 A | H | 2,4,6-trimethylphenyl | $-(CH_2)_2-$N-methylpyrrolidin-2-yl | Difumarate 140–4° C. (Et$_2$O) |
| 47 | 44832 A | H | 4-methylphenyl | $-(CH_2)_3-N(CH_3)_2$ | Dihydrochloride (0.5H$_2$O) 165° C. (Et$_2$O) |
| 48 | 44862 A | H | 4-fluorophenyl | $-(CH_2)_3-$N-methylpiperazin-1-yl | Trihydrochloride (1H$_2$O) 249–251° C. (Et$_2$O) |
| 49 | 44887 A | H | 2,4,6-trimethylphenyl | $-(CH_2)_3-N(CH(CH_3)_2)_2$ | Dihydrochloride (1.5H$_2$O) 78–82° C. (Et$_2$O) |
| 50 | 44907 A | H | " | $(CH_3)_2CH-CH_2-N(CH_3)_2$ (neopentyl-type) | Difumarate (0.5H$_2$O) 173–4° C. (Et$_2$O) |
| 51 | 44908 A | H | " | $-(CH_2)_2-N(CH(CH_3)_2)_2$ | Dihydrochloride 114–6° C. (Et$_2$O) |

TABLE 2-continued $$\underset{R_2}{\overset{R_1}{\diagdown}}C=C\underset{N}{\overset{S-NH-R_4}{\diagup}}$$

| Ex. no. | SR code no. | R$_1$ | R$_2$ | R$_4$ | Salt M.p. °C. (solvent) |
|---|---|---|---|---|---|
| 52 | 44914 A | H | 2,4-difluorophenyl | $-CH_2-C(CH_3)(CH_3)-CH_2N(CH_3)_2$ | Dihydrochloride 180–5° C. (Et$_2$O) |
| 53 | 44915 A | H | 2,4,6-trimethylphenyl | $-(CH_2)_3-N\underset{}{\diagdown}N-CH_3$ (piperazinyl) | Trihydrochloride 145–150° C. (Et$_2$O/iPrOH) |
| 54 | 44916 A | H | 2,4-difluorophenyl | $-(CH_2)_3N(CH(CH_3)_2)_2$ | Dihydrochloride 165–7° C. (iPrOH/Et$_2$O) |
| 55 | 44963 A | phenyl | —C$_2$H$_5$ | $-(CH_2)_3N(C_2H_5)_2$ | Dihydrochloride (1H$_2$O) 155–6° C. (acetone) |
| 56 | 44964 A | H | 2,4,6-trimethylphenyl | $-(CH_2)_3-N$(pyrrolidinyl) | Difumarate 147–8° C. (Et$_2$O) |
| 57 | 44965 A | H | " | 1-ethyl-3-piperidinyl | Fumarate (1H$_2$O) 226–8° C. (Et$_2$O) |
| 58 | 44967 A | phenyl | H | $-(CH_2)_3N(CH_3)_2$ | Dihydrochloride 82° C. (Et$_2$O) |
| 59 | 45001 A | H | 2-methylphenyl | $-(CH_2)_3N(CH_3)_2$ | Fumarate 123° C. (Et$_2$O) |
| 60 | 45015 A | phenyl | phenyl | " | Dihydrochloride (0.5H$_2$O) 210° C. (Et$_2$O) |

TABLE 2-continued $$R_1 \diagdown \overset{S}{\underset{R_2}{\diagup}} \diagdown \overset{NH-R_4}{\underset{N}{\diagdown}}$$

| Ex. no. | SR code no. | R₁ | R₂ | R₄ | Salt M.p. °C. (solvent) |
|---|---|---|---|---|---|
| 61 | 45016 A | 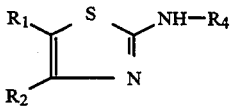 phenyl | 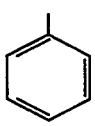 CH₂-phenyl | " | Dihydrochloride (0.5H₂O) 207–8° C. (Et₂O) |
| 62 | 45018 A | H | 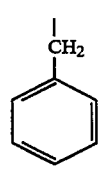 4-OCH₃-phenyl | " | Dihydrochloride (0.5H₂O) 165–7° C. (Et₂O) |
| 63 | 45023 A | H | 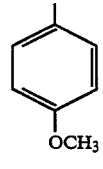 4-OH-phenyl | " | Dihydrochloride 238–240° C. (Et₂O) |
| 64 | 45030 A | H | 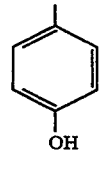 2,4,6-tri-CH₃-phenyl | —(CH₂)₃NHCH₃ | Difumarate 138–140° C. |
| 65 | 45035 A | H | 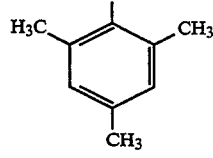 2,3,6-tri-CH₃-phenyl | —(CH₂)₃N(CH₃)₂ | Dihydrochloride (0.5H₂O) 222–5° C. (Et₂O) |
| 66 | 45038 A | H | 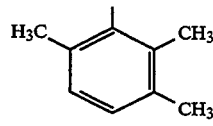 2,4-di-CH₃-phenyl | " | Trihemifumarate 129–130° C. (Et₂O) |
| 67 | 45043 A | 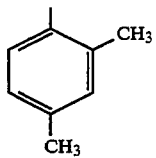 CH₂-phenyl | H | " | Trihemifumarate 102–3° C. (Et₂O) |
| 68 | 45079 A | H | 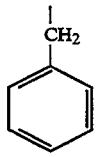 C(CH₃)₂-phenyl | " | Dihydrochloride (1H₂O) 130–2° C. (Et₂O) |

TABLE 2-continued $$\begin{array}{c} R_1 \\ \diagdown \\ R_2 \end{array} \begin{array}{c} S \\ \diagup \\ N \end{array} NH{-}R_4$$

| Ex. no. | SR code no. | $R_1$ | $R_2$ | $R_4$ | Salt M.p. °C. (solvent) |
|---|---|---|---|---|---|
| 69 | 45080 A | H | 2,6-dichlorophenyl | " | Dihydrochloride (0.5H$_2$O) 228° C. (Et$_2$O) |
| 70 | 45088 A | phenyl | —C$_2$H$_5$ | " | Trihemifumarate 125–6° C. (Et$_2$O) |
| 71 | 45107 A | H | —C(CH$_3$)$_2$-phenyl | —(CH$_2$)$_2$N(CH$_3$)$_2$ | Fumarate 114° C. (Et$_2$O) |
| 72 | 45108 A | H | 2,4,6-trimethylphenyl | —(CH$_2$)$_2$N(CH$_3$)$_2$ | Monohydrochloride (1H$_2$O) 202° C. (Et$_2$O) |
| 73 | 45125 A | H | " | —(CH$_2$)$_4$N(CH$_3$)$_2$ | Difumarate 132–3° C. (Et$_2$O) |
| 74 | 45137 A | —CH$_2$-phenyl | H | —(CH$_2$)$_2$N(CH$_3$)$_2$ | Monohydrochloride 183° C. (Et$_2$O) |
| 75 | 45154 A | H | 2,4,6-trimethylphenyl | —(CH$_2$)$_3$N(CH$_3$)(C$_2$H$_5$) | Difumarate 126–7° C. (Et$_2$O) |
| 76 | 45190 A | H | 2,4,5-trimethylphenyl | —(CH$_2$)$_3$N(CH$_3$)$_2$ | Difumarate (0.5H$_2$O) 116–8° C. (Et$_2$O) |
| 77 | 44813 A | H | 2,4,6-trimethylphenyl | —CH$_2$-(2-pyridyl) | Dihydrochloride 246–8° C. (Et$_2$O) |

TABLE 2-continued $$\begin{array}{c} R_1 \quad S \\ \diagdown \quad \diagup \\ \quad \quad \text{NH—}R_4 \\ \diagup \quad \diagdown \\ R_2 \quad N \end{array}$$

| Ex. no. | SR code no. | R₁ | R₂ | R₄ | Salt M.p. °C. (solvent) |
|---|---|---|---|---|---|
| 78 | 44833 A | H | 2,4-dichlorophenyl | " | Dihydrochloride 125–6° C. (Et₂O) |
| 79 | 44839 A | H | 2,4,6-trimethylphenyl (mesityl) | —CH₂-(3-pyridyl) | Dihydrochloride (0.5H₂O) 245° C. (Et₂O) |
| 80 | 44840 A | H | 4-fluorophenyl | —CH₂-(4-pyridyl) | Dihydrochloride (1H₂O) 219–220° C. (Et₂O) |
| 81 | 44856 A | H | 2,4,6-trimethylphenyl (mesityl) | —(CH₂)₂-(4-pyridyl) | Dihydrochloride 225–6° C. (Et₂O) |
| 82 | 44863 A | H | 4-chlorophenyl | —CH₂-(3-pyridyl) | Dihydrochloride (2H₂O) 111–2° C. (Et₂O) |
| 83 | 44864 A | H | 2,4,6-trimethylphenyl (mesityl) | —CH₂-(4-pyridyl) | Dihydrochloride (2H₂O) 237–9° C. (Et₂O) |
| 84 | 44902 A | phenyl | phenyl | —CH₂-(4-pyridyl) | Dihydrochloride (0.5H₂O) 183° C. (Et₂O) |
| 85 | 44903 A | H | 2,4-dichlorophenyl | —(CH₂)₂-(4-pyridyl) | Dihydrochloride 200–2° C. (Et₂O) |

TABLE 2-continued $$\begin{array}{c} R_1 \diagdown \quad S \diagdown \quad NH-R_4 \\ R_2 \diagup \quad \diagup N \end{array}$$

| Ex. no. | SR code no. | R₁ | R₂ | R₄ | Salt M.p. °C. (solvent) |
|---|---|---|---|---|---|
| 86 | 44904 A | phenyl | phenyl | —CH₂-(3-pyridyl) | Dihydrochloride (1H₂O) 133–5° C. (Et₂O) |
| 87 | 44905 A | H | 2,4,6-trimethylphenyl | —(CH₂)₂-(2-pyridyl) | Dihydrochloride (1.5H₂O) 122° C. (Et₂O) |
| 88 | 44906 A | phenyl | phenyl | —(CH₂)₂-(2-pyridyl) | Dihydrochloride (1H₂O) 173° C. (Et₂O) |
| 89 | 44913 A | H | 4-fluorophenyl | —(CH₂)₂-(2-pyridyl) | Monohydrochloride 171° C. (Et₂O) |
| 90 | 44911 A | phenyl | phenyl | —(CH₂)₂-(4-pyridyl) | Monohydrochloride 221° C. (Et₂O) |
| 91 | 44912 A | " | " | —CH₂-(2-pyridyl) | Monohydrochloride 150° C. (Et₂O) |
| 92 | 44966 A | phenyl | H | —(CH₂)₂-(4-pyridyl) | Fumarate 148° C. (Et₂O) |
| 93 | 44968 A | " | H | —CH₂-(3-pyridyl) | Fumarate 147–8° C. (Et₂O) |
| 94 | 44998 A | " | H | —(CH₂)₂-(2-pyridyl) | Dihydrochloride (1H₂O) 211° C. (Et₂O) |
| 95 | 45002 A | " | H | —CH₂-(4-pyridyl) | Dihydrochloride (2H₂O) 94° C. (Et₂O) |

TABLE 2-continued
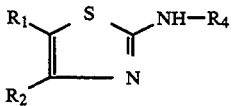
| Ex. no. | SR code no. | R₁ | R₂ | R₄ | Salt M.p. °C. (solvent) |
|---|---|---|---|---|---|
| 96 | 45106 A | H | 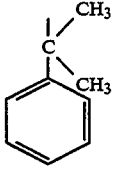 | 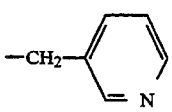 | Dihydrochloride 137° C. (Et₂O) |
| 97 | 45124 A | 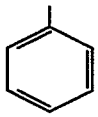 | C₂H₅ | 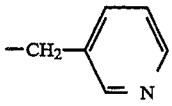 | Dihydrochloride 213–6° C. (Et₂O) |
| 98 | 45122 A | H | 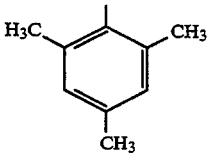 | 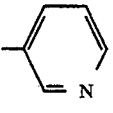 | Monohydrochloride >250° C. (Et₂O) |
| 99 | 45123 A | H | 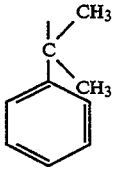 | " | Monohydrochloride 184° C. (Et₂O) |
| 100 | 45169 A | H | 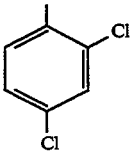 | 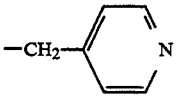 | Dihydrochloride 201–4° C. (iPrOH/EtOH) |
| 101 | 45185 A | 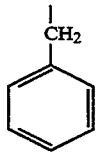 | H | 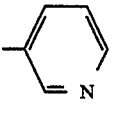 | Base (1H₂O) 163° C. (Et₂O) |
| 102 | 45221 A | H | 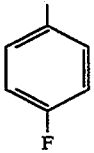 | —(CH₂)₂—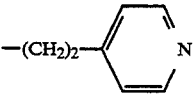 | Dihydrochloride 207–9° C. (iPrOH) |
| 103 | 45253 A | H | 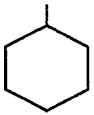 | —CH₂—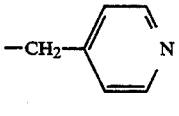 | Monohydrochloride 160° C. (Et₂O) |
| 104 | 45240 A | H | " | —CH₂—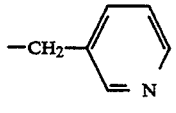 | Dihydrochloride 191–2° C. (Et₂O) |

TABLE 2-continued $$R_1\!\!-\!\!\underset{R_2}{\overset{S}{C}}\!=\!\underset{N}{C}\!-\!NH\!-\!R_4$$

| Ex. no. | SR code no. | R₁ | R₂ | R₄ | Salt M.p. °C. (solvent) |
|---|---|---|---|---|---|
| 105 | 45239 A | H | 2,4,6-trimethylphenyl (H₃C, CH₃, CH₃ substituted phenyl) | —(CH₂)₂—(3-pyridyl) | Dihydrochloride 227–9° C. (Et₂O) |
| 106 | 45255 A | H | phenyl | —CH₂—(4-pyridyl) | Monohydrochloride (0.5H₂O) 200–1° C. (Et₂O) |
| 107 | 45264 A | H | 2,4,6-trimethylphenyl (H₃C, CH₃, CH₃ substituted phenyl) | —(CH₂)₃—(2-pyridyl) | Dihydrochloride 221–3° C. (iPrOH/Et₂O) |
| 108 | 45258 A | H | " | —(CH₂)₃—NH—cyclopropyl | Oxalate 170–172° C. (acetone) | iPrOH = isopropanol;
PrOH = propanol;
EtOH 95 = 95° ethanol;
Et₂O = anhydrous ethyl ether;
iPr₂O = isopropyl ether

EXAMPLE 109:

2-[(3-Aminopropyl)amino]-5-methyl-4-phenylthiazole dihydrochloride (SR 44514 A)

A) 3-N-Boc-aminopropionitrile 56 ml of triethylamine are added to a solution of 26 g of 3-aminopropionitrile fumarate in 100 ml of water and the mixture is then heated to 50° C. A solution of 46 g of dicarbonic acid bis-tert.-butyl ester (Boc₂O) in 100 ml of dioxane is then added with vigorous stirring.

After evaporation of the solvent, the residue is taken up with methylene chloride. The organic solution is washed with a 5% aqueous solution of sodium carbonate and then with sulfate buffer of pH 2. The solution is dried over magnesium sulfate and the solvent is evaporated off. The residue (38.8 g) crystallizes.

B) 3-N-Boc-aminopropylamine 20 g of the above product are dissolved in a mixture of 400 ml of water, 40 ml of aqueous ammonia and 50 ml of ethanol. Raney nickel is added and the mixture is hydrogenated at ordinary temperature and pressure.

After the catalyst has been filtered off, the solvents are evaporated off in vacuo. The residue is taken up in an aqueous solution of sodium chloride and extracted with ethyl acetate. The solution is dried over magnesium sulfate and the solvent is evaporated off to give 12.6 g of the expected product.

C) N-Benzoyl-N'-(3-N-Boc-aminopropyl)thiourea

A solution of 6.38 ml of benzoyl chloride in 20 ml of anhydrous acetone is added dropwise to a suspension of 7.05 g of potassium thiocyanate in 50 ml of anhydrous acetone and the mixture is then refluxed for 5 minutes.

A solution of 12.6 g of 3-N-Boc-aminopropylamine in 20 ml of methylene chloride is added slowly to the hot solution, with vigorous stirring.

When the addition is complete, the mixture is stirred for 1 hour, the solvents are then evaporated off and the residue is taken up in iced water. Extraction is carried out with ethyl acetate and the solution is dried over magnesium sulfate. The solvent is evaporated off and the residue is taken up in 100 ml of cold anhydrous ether.

The crystals formed are filtered off, washed with cold ether and dried in an oven at 70° C.

Weight: 8.3 g; m.p.; 104°–105° C.

D) SR 44514 A 3.37 g of the product obtained above are refluxed in 14 ml of a 2.5N solution of sodium hydroxide for 15 minutes.

After cooling, concentrated hydrochloric acid is added until the pH is 1. A solution of 2.13 g of 2-bromopropiophenone in 20 ml of ethanol is added and the mixture is refluxed for 1 hour under a nitrogen atmosphere.

The mixture is treated as indicated in Example 1-B to give an oil.

The dihydrochloride is formed in solution in methanol by the addition of a solution of hydrogen chloride in ether.

M.p.: 100°–110° C.

EXAMPLES 110 AND 111:

The following are obtained in the same way, starting from the substituted thiourea prepared in Example 109-C and following the procedure of Example 109-D but varying the bromine derivative used:

Example 110

2-[(3-Aminopropyl)amino]-4-(4-fluorophenyl)thiazole (SR 44886 A) isolated in the form of the fumarate (0.5H$_2$O). M.p.: 162°–4° C.

EXAMPLE 111

2-[(3-Aminopropyl)amino]-4-(2,4,6-trimethylphenyl)-thiazole (SR 44949 A) isolated in the form of the fumarate. M.p.: 163°–4° C.

EXAMPLE 112:

2-[N-Methyl-N-(pyridyl-3-methyl)amino]-4-(2,4,6-trimethylphenyl)thiazole oxalate (SR 45206 A)

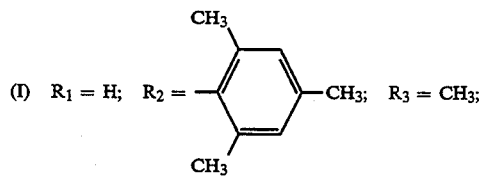

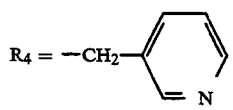

A) N-Methyl-N-(pyridyl-3-methyl)thiourea 24.6 ml of pivaloyl chloride are added dropwise, with thorough stirring, to a suspension of 16.2 g of sodium thiocyanate in 90 ml of anhydrous acetone, cooled to +4° C. The mixture is stirred for 3 hours at +4° C. and 25 g of 3-methylaminomethylpyridine are then added dropwise so as to keep the temperature between 0° and +4° C. The temperature is allowed to rise to 20° C. and the mixture is stirred for 15 hours at this temperature. It is evaporated in vacuo and the residue is taken up in 100 ml of concentrated hydrochloric acid. The solution is heated at 95° C. for 1 hour. After cooling, extraction is carried out twice with methylene chloride and the aqueous phase is then rendered alkaline with a concentrated solution of sodium hydroxide. Extraction is carried out 4 times with 200 ml of methylene chloride. The organic extracts are combined and dried over magnesium sulfate. The solvent is evaporated off and the residue crystallizes. The crystals are triturated with 100 ml of ether and filtered off. After drying, 26.7 g of the expected compound are obtained. M.p.: 119°–120° C.

B) SR 45206 A

A mixture of 3.6 g of the thiourea prepared above, 6 g of 2,4,6-trimethylphenacyl bromide, 20 ml of water, 50 ml of ethanol and 2 ml of concentrated hydrochloric acid is refluxed for 4 hours.

After evaporation in vacuo, the residue is taken up in 150 ml of methylene chloride and extraction is carried out with 150 ml of a 1N aqueous solution of hydrochloric acid. The organic phase is re-extracted 3 times with 100 ml of 1N hydrochloric acid and the acid extracts are combined. They are rendered alkaline with sodium hydroxide solution and extracted 4 times with 150 ml of methylene chloride. The organic extracts are combined and dried over magnesium sulfate and the solvent is evaporated off. The oily residue is chromatographed on a silica column (100 g). Elution with a 97/3 vol/vol methylene chloride/methanol mixture gives 4.5 g of oily product.

OXALATE

The 4.5 g of the above product are dissolved in 30 ml of acetone and a solution of 1.4 g of oxalic acid in 40 ml of acetone is added.

The pale yellow crystals formed are filtered off, washed with a small volume of acetone and dried.

4.3 g of the expected product are obtained. M.p.: 160°–1° C.

EXAMPLES 113 TO 117:

The substituted thioureas collated in Table 3 are obtained in the same way by following the procedure of Example 112-A.

TABLE 3

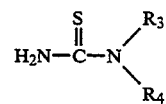

| $\overset{R_3}{\underset{R_4}{N}}$ | Melting point |
|---|---|
| −N⟨N−CH$_3$⟩ (piperazine) | M.p.: 174–5° C. |
| −N(C$_2$H$_5$)(CH$_2$)$_3$N(CH$_3$)CH$_3$ | M.p.: 40–4° C. |
| −N(CH$_3$)⟨N−CH$_3$⟩ (piperazine) | M.p.: 141–3° C. |

B) The compound I in Table 4 are obtained from these different thioureas by following the procedure of Example 112-B.

EXAMPLES 119 TO 124:

The products of formula (I) collated in Table 5 are obtained by following the procedure of Example 118 but varying the bromine derivatives and/or the benzoylthioureas.

TABLE 4

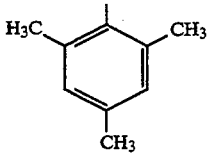

| Ex. no. | SR code no. | R₁ | R₂ | NR₃R₄ | Salt isolated Melting point °C. |
|---|---|---|---|---|---|
| 113 | 45215 A | H | 2,4,6-trimethylphenyl | —N(piperazinyl)N—CH₃ | Monohydrochloride (1H₂O) 145–7° C. (Et₂O) |
| 114 | 45216 A | H | —CH₂—C₆H₅ | " | Monohydrochloride 210–1° C. (Et₂O) |
| 115 | 45223 A | H | —C(CH₃)₂—C₆H₅ | " | Dihydrochloride 231–2° C. (Et₂O) |
| 116 | 45191 A | H | 2,4,6-trimethylphenyl | —N(C₂H₅)—(CH₂)₃—N(CH₃)₂ | Oxalate 44–5° C. |
| 117 | 45257 A | H | " | —N(CH₃)(piperidinyl-N—CH₃) | Dihydrochloride 224–6° C. (iPrOH/iPr₂O) |

EXAMPLE 118:

2-(2-Morpholinoethylamino)-4,5-dihydronaphtho[1,2-d]thiazole dihydrochloride (SR 44273 A)

3.66 g of N-benzoyl-N'-(morpholinoethyl)thiourea are refluxed in 17.5 ml of a 2.5N solution of sodium hydroxide under a nitrogen atmosphere for 15 minutes. After cooling, concentrated hydrochloric acid is added until the pH is 7. A solution of 3 g of 2-bromo-1,2,3,4-tetrahydronaphthalen-1-one in 20 ml of ethanol is added and the mixture is refluxed for 1 hour. After evaporation of the solvent, the residue is neutralized by the addition of sodium bicarbonate and extraction is carried out twice with methylene chloride. The organic phase is dried over magnesium sulfate and chromatographed on a silica column by elution with a methylene chloride/methanol mixture (95/5 vol/vol).

After evaporation of the solvents, the oily residue is taken up in ether and the hydrochloride is precipitated in ether. It is filtered off and recrystallized from an isopropanol/95° ethanol mixture.

M.p.: 255°–257° C.

TABLE 5

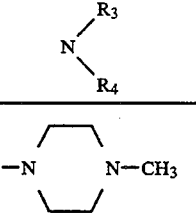

| Ex. no. | SR code no. | m | n | NR₆R₇ | Salt M.p. °C. (solvent) |
|---|---|---|---|---|---|
| 119 | 44317 A | 3 | 2 | —N(morpholino)O | Dihydrochloride 217 (iPrOH/EtOH 95) |

TABLE 5-continued

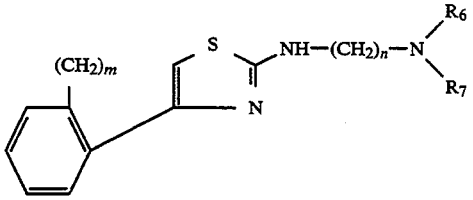

| Ex. no. | SR code no. | m | n | −N(R6)(R7) | Salt M.p. °C. (solvent) |
|---|---|---|---|---|---|
| 120 | 44323 A | 3 | 2 | −N(C2H5)(C2H5) | Dihydrochloride 170 (iPrOH/Et2O) |
| 121 | 44326 A | 3 | 3 | " | Dihydrochloride 0.5H2O 192 (iPrOH/iPr2O) |
| 122 | 44327 A | 3 | 3 | −N(CH3)(CH3) | Dihydrochloride 1H2O 198 (Et2O) |
| 123 | 44392 A | 3 | 3 | −N(morpholino) | Dihydrochloride 0.5H2O 245 dec (Et2O) |
| 124 | 44393 A | 2 | 2 | −N(C2H5)(C2H5) | Dihydrochloride 0.5H2O 181 (Et2O/PrOH) |

EXAMPLE 125:

2-[(2-Diethylaminoethyl)amino]-9-nitro-5,6-dihydro-4H-benzo[6,7]cyclohepta[1,2-d]thi azole dihydrochloride (SR 44411 A)

The procedure of Example 118 is followed using N-benzoyl-N'-(3-diethylaminopropyl)thiourea and 2-bromo-8-nitrobenzocycloheptan-1-one as the starting materials.

The expected product is obtained in the same way in the form of the dihydrochloride.

M.p.: 192°–195° C. (isopropanol/95° ethanol).

The products according to the invention were studied for their pharmacological properties and in particular for their affinity for muscarinic cholinergic receptors.

The study was carried out by means of in vitro biochemical tests and also by means of pharmacological tests performed on animals.

IN VITRO BIOCHEMICAL STUDY

There are two subclasses of muscarinic cholinergic receptors in mammals: the $M_1$ and $M_2$ receptors.

The $M_1$-type receptors are concentrated in certain regions of the brain, such as the hippocampus, the cerebral cortex and the striatum, and also in the sympathetic ganglia. These binding sites can be selectively labeled with tritiated pirenzepine ($^3$H-PZ). The $M_2$-type receptors predominate in the heart and the ileum and can be labeled with tritiated N-methyl-scopolamine ($^3$H-NMS). The selectivity of the products of the invention with respect to the $M_1$ and $M_2$ sites was determined by studying their in vitro interaction with $^3$H-PZ and $^3$H-NMS firmly bound with a high affinity to rat hippocampus membranes and smooth guinea-pig ileum muscle, respectively.

Methodologies

A) Testing for affinity for the $M_1$-type muscarinic cholinergic receptor

The interaction of the molecules with the $M_1$-type muscarinic receptors was studied by in vitro measurement, on a rat hippocampus homogenate, of the displacement of tritiated pirenzepine from its specific binding sites. Aliquots (10 μl) of a 5% (w/v) rat hippocampus homogenate in an $Na_2HPO_4$ buffer (50 mM, pH 7.40) are incubated for 2 hours at 4° C. in the presence of $^3$H-PZ (76 Ci/mmol; final concentration 1 nM) and increasing concentrations of the test product. The final volume is 2 ml. The reaction is stopped by centrifugation for 10 minutes at 50,000×g. After decantation and washing of the residues, the bound radioactivity is counted by liquid scintillation. The non-specific binding is determined in the presence of 10 μM atropine sulfate. The 50% inhibitory concentration ($IC_{50}$) is determined graphically. (Ref.: J. D. Watson, W. R. Roeskoe and H. I. Yamamura, Life Sci., 1982, 31, 2019–2029.)

B) Testing for affinity for the $M_2$-type muscarinic cholinergic receptor

The interaction with the $M_2$-type muscarinic receptors was studied by in vitro measurement, on a smooth guinea-pig ileum muscle homogenate, of the displacement of tritiated N-methylscopolamine from its specific binding sites. Aliquots (50 μl) of a 0.625% (w/v) smooth guinea-pig ileum muscle homogenate in 20 mM HEPES buffer—2-(2-hydroxy-4-ethylpiperazin-1-yl)ethanesulfonic acid containing NaCl (100 mM) and $MgCl_2$ (10 mM) (final pH: 7.5)—are incubated for 20 minutes at 30° C. in the presence of $^3$H-NMS (85 Ci/mmol; final concentration 0.3 nM) and increasing concentrations of the test products. The final volume is 1 ml. The reaction is stopped by centrifugation for 5 minutes at 15,000×g. The non-specific binding is determined in the presence of 10 mM atropine sulfate. (Ref.: R. Hammer et al., Nature, 1980, 283, 90–92; E. C. Hulme et al., Mol. Pharmacol., 1978, 14, 737–750.)

Results

Table 6 indicates the affinities of the products of the invention for the $M_1$ and $M_2$ receptors. The results are expressed as 50 per cent inhibitory concentrations ($IC_{50}$), i.e. the concentration (in μM) which induces the displacement of 50% of the tritiated ligand bound to the membrane receptors. The $IC_{50}$ for $^3$H-PZ displacement represents the affinity for the $M_1$ receptor; the $IC_{50}$ for $^3$H-NMS displacement represents the affinity for the $M_2$ receptor.

Also, the next column of the table indicates the ratio R of the $IC_{50}$ values for the $M_1$ and $M_2$ receptors, which expresses the selectivity of the products with respect to one of the receptor types.

By way of comparison, Table 6 indicates the results obtained with 3 reference products.

TABLE 6

| Product no. | ³H-PZ(M₁) IC₅₀ μM | ³H-NMS(M₂) IC₅₀ μM | $R = \frac{IC_{50}(M_2)}{IC_{50}(M_1)}$ |
|---|---|---|---|
| SR 44284 A | 8 | 40 | 5 |
| SR 44286 A | 6 | 100 | 16 |
| SR 44318 A | 3.4 | 38 | 11 |
| SR 44323 A | 1.7 | 8.5 | 5 |
| SR 44326 A | 2.2 | >100 | >45 |
| SR 44327 A | 1.9 | 38 | 20 |
| SR 44345 A | 1 | 70 | 70 |
| SR 44346 A | 2 | 25 | 12.5 |
| SR 44347 A | 0.35 | 13 | 37 |
| SR 44372 A | 0.12 | 5 | 41 |
| SR 44373 A | 0.70 | 15 | 21 |
| SR 44374 A | 0.40 | 8 | 20 |
| SR 44393 A | 2.7 | 42 | 15 |
| SR 44411 A | 0.9 | 6.7 | 7 |
| SR 44421 A | 3.6 | >100 | >27 |
| SR 44422 A | 8.1 | 100 | 12 |
| SR 44423 A | 6.4 | 100 | 15 |
| SR 44434 A | 1.5 | 70 | 46 |
| SR 44435 A | 0.36 | 3 | 8 |
| SR 44436 A | 1.7 | 50 | 29 |
| SR 44437 A | 0.43 | 3 | 7 |
| SR 44438 A | 1 | 60 | 60 |
| SR 44451 A | 6 | 80 | 13 |
| SR 44465 A | 2.6 | 40 | 15 |
| SR 44467 A | 1.5 | 38 | 25 |
| SR 44468 A | 1.2 | 22 | 18 |
| SR 44469 A | 2.6 | 60 | 23 |
| SR 44488 A | 1.7 | 34 | 20 |
| SR 44489 A | 0.3 | 2 | 6 |
| SR 44490 A | 1.5 | 25 | 16 |
| SR 44491 A | 0.8 | 8.5 | 10 |
| SR 44492 A | 3.6 | 28 | 8 |
| SR 44493 A | 1.6 | 45 | 28 |
| SR 44494 A | 0.8 | 80 | 100 |
| SR 44514 A | 0.5 | >100 | >200 |
| SR 44515 A | 0.2 | 3.4 | 17 |
| SR 44516 A | 3.4 | 75 | 22 |
| SR 44573 A | 1.8 | 13 | 7 |
| SR 44574 A | 0.2 | 24 | 120 |
| SR 44575 A | 7 | >100 | >14 |
| SR 44749 A | 1.8 | 26 | 14 |
| SR 44769 A | 2 | 30 | 15 |
| SR 44770 A | 0.6 | 26 | 43 |
| SR 44786 A | 0.6 | 40 | 67 |
| SR 44791 A | 5 | 40 | 8 |
| SR 44792 A | 1.8 | 30 | 17 |
| SR 44813 A | 6 | >100 | >17 |
| SR 44814 A | 1.4 | 10 | 7 |
| SR 44832 A | 2.4 | >100 | >42 |
| SR 44839 A | 0.4 | 100 | 250 |
| SR 44840 A | 0.6 | >100 | >167 |
| SR 44856 A | 0.3 | >100 | >300 |
| SR 44862 A | 3 | 34 | 11 |
| SR 44864 A | 0.28 | >100 | >360 |
| SR 44886 A | 6.3 | 70 | 11 |
| SR 44904 A | 6 | >100 | >17 |
| SR 44905 A | 2.4 | 60 | 25 |
| SR 44906 A | 2.4 | >100 | >42 |
| SR 44908 A | 0.13 | 4 | 31 |
| SR 44915 A | 0.4 | 40 | 100 |
| SR 44916 A | 0.13 | 5 | 38 |
| SR 44963 A | 0.12 | 6 | 50 |
| SR 44964 A | 0.9 | 28 | 31 |
| SR 44965 A | 1.2 | 60 | 50 |
| SR 44966 A | 4.5 | 100 | 22 |
| SR 44967 A | 1.8 | 40 | 22 |
| SR 45001 A | 2.60 | 30 | 11 |
| SR 45015 A | 0.3 | 4 | 13 |
| SR 45016 A | 0.10 | 5.5 | 55 |
| SR 45030 A | 1.60 | 80 | 50 |
| SR 45106 A | 3 | >100 | >33 |
| Oxotremorine | 0.24 | 0.2 | 1 |
| Arecoline | 17 | 4.5 | 0.3 |
| Pilocarpine | 2.5 | 7 | 3 |

The results show that the compounds according to the invention have a strong affinity for muscarinic cholinergic receptors, with a marked specificity for the M₁-type central receptors.

IN VIVO PHARMACOLOGICAL STUDY

Pirenzepine (PZ) is a specific antagonist of the $M_1$ central muscarinic cholinergic receptors. The intrastriatal injection of PZ into mice induces rotatory behavoir. The antagonism of this behavoir by the products according to the invention was studied.

The products according to the invention are administered either intraperitoneally (i.p.) or orally (p.o.) after solubilization in distilled water or suspension in a 5% solution of gum arabic. The control animals receive the pure solvent under the same conditions.

The animals used are female mice (Swiss, CD 1, Charles River, France) with a body weight of between 25 and 30 grams.

The pirenzepine is dissolved in a phosphate buffer and the pH of the solution is 6.

The test products or their solvents are administered in a volume of 0.4 ml per 20 g of body weight, either by i.p. injection or orally via an esophageal tube. Administration takes place either 15 minutes (i.p.) or 30 minutes (p.o.) before a direct injection of pirenzepine into the right striatum of the mouse at a dose of 1 μg in 1 μl of solvent, according to the method described by P. WORMS et al. in Eur. J. Pharmacol., 1986, 121, 395-401.

The number of contralateral rotations (rotations in the opposite direction to the side injected) was counted for three 2-minute periods after injection of the pirenzepine: 2nd to 4th, 8th to 10th and 13th to 15th minutes. Each treatment consists of 3 to 4 doses and 10 animals per dose. The total number of rotations and the percentage antagonism with respect to the control group are calculated for each treatment.

The 50% effective dose (ED₅₀), i.e. the dose which causes a 50% reduction in the number of rotations induced by pirenzepine, is determined graphically for each product. The results are reported in Table 7.

Table 7 indicates, for each product tested, the 50% effective dose (ED₅₀) in mg/kg in mice for the antagonism of the rotations induced by pirenzepine, either by i.p. administration or by oral administration.

By way of comparison, the results obtained with 3 reference products have been reported.

TABLE 7

| Product no. | Pirenzepine antagonism ED₅₀ mg/kg i.p. | Pirenzepine antagonism ED₅₀ mg/kg p.o. |
|---|---|---|
| SR 44244 A | 8 | 20 |
| SR 44284 A | 8 | — |
| SR 44285 A | 3 | — |
| SR 44286 A | 3 | 10 |
| SR 44318 A | 1.5 | 3 |
| SR 44323 A | 10 | — |
| SR 44326 A | 3 | — |
| SR 44327 A | 10 | — |
| SR 44345 A | 0.5 | 1 |
| SR 44346 A | 1 | — |
| SR 44347 A | 0.03 | 0.20 |
| SR 44372 A | 1 | 3 |
| SR 44373 A | 0.3 | 1 |
| SR 44374 A | 3 | — |
| SR 44392 A | 3 | — |
| SR 44393 A | 3 | — |
| SR 44411 A | 15 | — |
| SR 44421 A | — | 0.2 |
| SR 44435 A | 2 | — |
| SR 44467 A | — | 3 |
| SR 44493 A | — | 0.3 |

TABLE 7-continued

| Product no. | Pirenzepine antagonism ED$_{50}$ mg/kg i.p. | Pirenzepine antagonism ED$_{50}$ mg/kg p.o. |
|---|---|---|
| SR 44494 A | — | 2 |
| SR 44514 A | 3 | — |
| SR 44573 A | — | 2.50 |
| SR 44749 A | — | 3 |
| SR 44770 A | — | 3 |
| SR 44792 A | — | 3 |
| SR 44814 A | — | 0.2 |
| SR 44839 A | — | 0.2 |
| SR 44856 A | — | 3 |
| SR 44862 A | — | 3 |
| SR 44887 A | — | 0.3 |
| SR 44915 A | — | 3 |
| SR 44949 A | — | 10 |
| SR 44964 A | — | 3 |
| SR 44965 A | — | 3 |
| SR 45001 A | — | 3 |
| SR 45015 A | — | 0.70 |
| SR 45016 A | — | 2 |
| SR 45030 A | — | 1 |
| Oxotremorine* | 0.005 | — |
| Arecoline* | 1 | 0.5 |
| Pilocarpine* | 1 | 10 |

*Strong induction of side-effects (trembling, salivation, lacrimation, defecation, piloerection, hypothermia, sedation) at doses close to the active doses in these tests.

The results in Table 7 show that the compounds according to the invention are active in stimulating central cholinergic transmission and are therefore capable of being used as agonists of muscarinic receptors.

Furthermore, some of the products according to the invention displayed an antagonistic activity towards the effect of excitatory amino acids in the brain. This activity was measured in the test for the release of acetylcholine caused by N-methyl-D-aspartic acid (NMDA) on sections of rat striatum (J. Lehmann and B. Scatton, Brain Research 1982, 252, 77–89).

Finally, the acute toxicity was determined for various products according to the invention. The products were administered intraperitoneally in increasing doses to groups of 10 female mice (Swiss, CD 1, Charles River, France) with a body weight of 20 g.

The mortality caused by the products studied was noted for 24 hours following administration of the product. The 50% lethal dose (LD$_{50}$), i.e. the dose which causes the death of 50% of the animals, was determined for each of the products.

The results obtained are collated in Table 8 below.

TABLE 8

| Product no. | LD$_{50}$ (mg/kg) i.p. |
|---|---|
| SR 44244 A | 250 |
| SR 44273 A | >100 |
| SR 44284 A | 450 |
| SR 44286 A | 200 |
| SR 44345 A | 200 |
| SR 44347 A | 60 |
| SR 44372 A | 75 |
| SR 44373 A | 75 |
| SR 44374 A | 150 |

The products according to the invention therefore have a low toxicity and show no signs of toxicity for the doses at which they are active.

Consequently, the compounds (I) can be used as drugs.

The results indicated above make it possible to consider using the products according to the invention for treating degenerative syndromes associated with senescence, and especially memory disorders and senile dementia.

According to another of its aspects, the present Application therefore relates to pharmaceutical compositions which contain at least one of the compounds of formula (I) or one of their salts as the active ingredient.

In the pharmaceutical compositions of the present invention for oral, sublingual, percutaneous or rectal administration, the active ingredients of formula I above can be administered to humans in single dosage forms, mixed with the conventional pharmaceutical excipients, especially for the treatment of senile dementia. The appropriate unit dosage forms include oral dosage forms, such as tablets, gelating capsules, powders, granules and solutions or suspensions to be taken orally, sublingual and buccal dosage forms, subcutaneous, intramuscular or intravenous dosage forms and rectal dosage forms.

To achieve the desired effect, the dose of active principle can vary between 20 and 500 mg per day.

Each unit dose can contain from 5 to 200 mg of active ingredient combined with a pharmaceutical excipient. This unit dose can be administered 1 to 4 times per day.

When a solid composition is prepared in the form of tablets, the main active ingredient is mixed with a pharmaceutical vehicle such as gelatin, starch, lactose, magnesium stearate, talc, gum arabic or the like. The tablets can be coated with sucrose or other appropriate substances, or else they can be treated so as to have a sustained or delayed activity and continuously release a predetermined amount of active principle.

A preparation in the form of gelatin capsules is obtained by mixing the active ingredient with a diluent and pouring the resulting mixture into soft or hard gelatin capsules.

Water-dispersible granules or powders can contain the active ingredient mixed with dispersants or wetting agents, or suspending agents such as polyvinylpyrrolidone, and with sweeteners or taste correctors.

For rectal administration, suppositories are used; these are prepared with binders which melt at the temperature of the rectum, for example cacao butter or polyethylene glycols.

For parenteral administration, aqueous suspensions, isotonic salt solutions or solutions which are sterile and injectable are used; these contain pharmacologically compatible dispersants and/or wetting agents, for example propylene glycol or butylene glycol.

The active principle can also be formulated as microcapsules, together with one or more excipients or additives if appropriate.

As an example of a pharmaceutical preparation, it is possible to prepare gelatin capsules containing:

| SR 44421 A | 0.010 g |
|---|---|
| lactose | 0.050 g |
| magnesium stearate | 0.005 g | by intimately mixing the above ingredients and pouring the mixture into hard gelatin capsules.

What is claimed is:

1. An aminothiazole derivative having the formula:

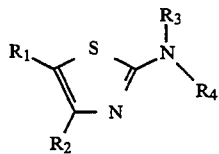

wherein

R₁ and R₂, taken together, represent a group:

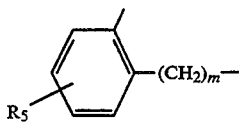

in which the phenyl group is bonded to the 4-position of the thiazole and the group $(CH_2)_m$ to the 5-position, and in which m represents an integer equal to 2 or 3, and $R_5$ denotes H or nitro occupying one of the free positions on the ring;

-$R_3$ represents H or $C_1$-$C_4$ lower alkyl; and
-$R_4$ represents:
- a group:

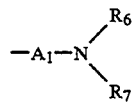

in which $A_1$ denotes linear or branched $C_2$-$C_5$ alkyl, and $R_6$ and $R_7$, taken independently, represent H, $C_1$-$C_4$ alkyl or $C_3$-$C_6$ cycloalkyl, or alternatively $R_6$ and $R_7$, taken with the nitrogen atom to which they are bonded, form a 5-membered or 6-membered heterocycle containing one or two nitrogen atoms as ring members or a nitrogen atom and an oxygen atom as ring members;
- a group:

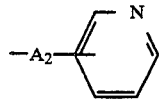

in which $A_2$ denotes a group $(CH_2)_{m'}$ where $m'=0$, 1, 2 or 3, which is bonded to the pyridine ring in the 2-, 3- or 4-position;
- a group:

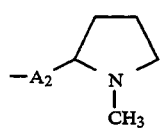

in which $A_2$ denotes a group $(CH_2)_{m'}$ $m'=0$, 1, 2 or 3; or
- a group:

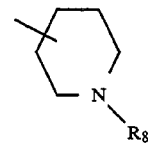

in which $R_8$ denotes $C_1$-$C_4$ alkyl; or alternatively the substituent $$-\overset{R_3}{\underset{}{N}}-R_4$$

represents a group:

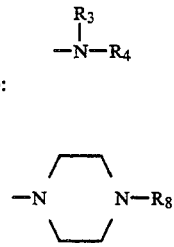

in which $R_8$ denotes $C_1$-$C_4$ alkyl;
or an addition salt thereof with a pharmaceutically acceptable mineral or organic acid.

2. An aminothiazole derivative as claimed in claim 1, wherein $R_4$ represents a group:

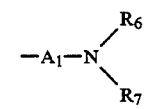

in which $A_1$ denotes a linear or branched $C_2$-$C_5$ alkyl group and $R_6$ and $R_7$, taken independently, represent hydrogen, a $C_1$-$C_4$ alkyl group or a $C_3$-$C_6$ cycloalkyl group, or alternatively $R_6$ and $R_7$, taken with the nitrogen atom to which they are bonded, form a 5-membered or 6-membered heterocycle containing one or two nitrogen atoms as ring members or a nitrogen atom and an oxygen atom as ring members.

3. An aminothiazole derivative as claimed in claim 2, wherein $R_6$ and $R_7$ represent a $C_1$-$C_4$ alkyl group.

4. An aminothiazole derivative as claimed in claim 2, wherein $R_6$ and $R_7$, taken with the nitrogen atom to which they are bonded, form a pyrrolidine, piperidine, morpholine or N-alkyl-piperazine ring.

5. An aminothiazole derivative as claimed in claim 4, wherein $R_6$ and $R_7$, taken with the nitrogen atom to which they are bonded, form a morpholine ring.

6. An aminothiazole derivative as claimed in claim 1, in which $R_4$ represents a group:

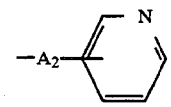

in which $A_2$ denotes a group $(CH_2)_{m'}$ where $m'=0$, 1, 2 or 3, which is bonded to the pyridine ring in the 2-, 3- or 4-position.

7. An aminothiazole derivative as claimed in claim 1, in which $R_4$ represents a group:

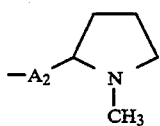

in which $A_2$ denotes a group $(CH_2)_{m'}$ where $m'=0$, 1, 2 or 3.

8. A pharmaceutical composition comprising an amount, effective for stimulating cholinergic transmission in a person suffering from memory disorder or senile dementia, of an aminothiazole derivative according to claim 1; and a pharmaceutically acceptable vehicle.

9. A pharmaceutical composition as claimed in claim 6, wherein said amount of aminothiazole derivative is from 20 to 500 mg.

10. A method of treating a patient suffering from a memory disorder or senile dementia, comprising administering to said patient in need of such treatment an amount effective for stimulating cholinergic transmission of an aminothiazole derivative having the formula:

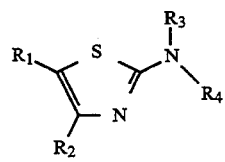

wherein $R_1$ and $R_2$, taken together, represent a group:

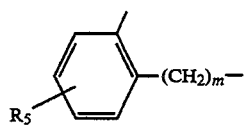

in which the phenyl group is bonded to the 4-position of the thiazole and the group $(CH_2)_m$ to the 5-position, and in which m represents an integer equal to 2 or 3, and $R_5$ denotes H or nitro occupying one of the free positions on the ring;

-$R_3$ represents H or $C_1$-$C_4$ lower alkyl; and
-$R_4$ represents:
- a group:

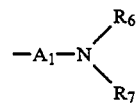

in which $A_1$ denotes linear or branched $C_2$-$C_5$ alkyl, and $R_6$ and $R_7$, taken independently, represent H, $C_1$-$C_4$ alkyl or $C_3$-$C_6$ cycloalkyl, or alternatively $R_6$ and $R_7$, taken with the nitrogen atom to which they are bonded, form a 5-membered or 6-membered heterocycle containing one or two nitrogen atoms as ring members or a nitrogen atom and an oxygen atom as ring members;
- a group:

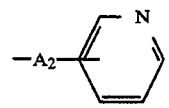

in which $A_2$ denotes a group $(CH_2)_{m'}$ where $m'=0$, 1, 2 or 3, which is bonded to the pyridine ring in the 2-, 3- or 4-position;
- a group:

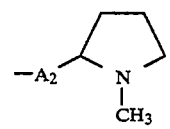

in which $A_2$ denotes a group $(CH_2)_{m'}$ where $m'=0$, 1, 2 or 3; or
- a group:

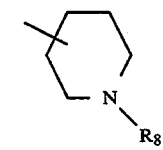

in which $R_8$ denotes $C_1$-$C_4$ alkyl; or alternatively the substituent

represents a group:

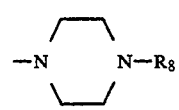

in which $R_8$ denotes $C_1$-$C_4$ alkyl;
or an addition salt thereof with a pharmaceutically acceptable mineral or organic acid.

* * * * *